(12) United States Patent
Schneider

(10) Patent No.: US 10,271,712 B2
(45) Date of Patent: Apr. 30, 2019

(54) METHOD AND DEVICE FOR CONTROLLING A COMPUTER PROGRAM BY MEANS OF AN INTRAORAL SCANNER

(71) Applicant: DENTSPLY SIRONA INC., York, PA (US)

(72) Inventor: Sascha Schneider, Muhltal (DE)

(73) Assignee: DENTSPLY SIRONA Inc., York, PA (US)

( * ) Notice: Subject to any disclaimer, the term of this patent is extended or adjusted under 35 U.S.C. 154(b) by 913 days.

(21) Appl. No.: 14/770,569

(22) PCT Filed: Feb. 28, 2014

(86) PCT No.: PCT/EP2014/053903
§ 371 (c)(1),
(2) Date: Aug. 26, 2015

(87) PCT Pub. No.: WO2014/131866
PCT Pub. Date: Sep. 4, 2014

(65) Prior Publication Data
US 2016/0000537 A1    Jan. 7, 2016

(30) Foreign Application Priority Data

Feb. 28, 2013    (DE) .................... 10 2013 203 449

(51) Int. Cl.
*G06F 17/50*        (2006.01)
*A61B 1/00*         (2006.01)
(Continued)

(52) U.S. Cl.
CPC ...... *A61B 1/00006* (2013.01); *A61B 1/00039* (2013.01); *A61B 1/24* (2013.01);
(Continued)

(58) Field of Classification Search
CPC ..................... A61C 9/004; A61B 1/00006
(Continued)

(56) References Cited

U.S. PATENT DOCUMENTS

2006/0243807 A1    11/2006    Tien
2007/0092854 A1    4/2007    Powell et al.
(Continued)

FOREIGN PATENT DOCUMENTS

DE        19534998 A1    3/1997
EP        2301330 A1     3/2011
(Continued)

OTHER PUBLICATIONS

International Search Report dated Jun. 17, 2014, in PCT Application No. PCT/EP2014/053903, 3 pp.
(Continued)

*Primary Examiner* — Hugh M Jones
(74) *Attorney, Agent, or Firm* — Dentsply Sirona Inc.

(57) ABSTRACT

The present invention relates to a computer program and to a method for controlling the computer program, wherein a control signal is sent to the computer program when an optical marker, in particular a two-dimensional barcode (2a, 2b, 2c), is detected by an intraoral scanner (1), which signal switches the computer program to a predefined state. A device for controlling the computer program comprises a support (3) on which at least one optical marker is arranged. The optical marker has an inscription (21a, 21b, 21c) which indicates a state of the computer program to which the computer program can be switched by detection of the optical marker by the intraoral scanner (1).

19 Claims, 4 Drawing Sheets

(51) Int. Cl.
    *A61C 9/00*      (2006.01)
    *A61B 1/24*      (2006.01)
    *A61B 90/94*     (2016.01)
    *G16H 50/50*     (2018.01)
    *G06F 19/00*     (2018.01)

(52) U.S. Cl.
    CPC ............ *A61B 90/94* (2016.02); *A61C 9/0053* (2013.01); *G06F 19/00* (2013.01); *G16H 50/50* (2018.01); *A61C 2204/005* (2013.01)

(58) Field of Classification Search
    USPC .......................................................... 703/6, 1
    See application file for complete search history.

(56) References Cited

U.S. PATENT DOCUMENTS

2008/0153067 A1    6/2008    Berckmans et al.
2009/0317757 A1    12/2009   Lemchen
2011/0076647 A1    3/2011    Ditzel et al.

FOREIGN PATENT DOCUMENTS

JP      2002041199 A    2/2002
WO         98/20411 A1  5/1998
WO      2012035444 A2   3/2012

OTHER PUBLICATIONS

International Preliminary Report on Patentability dated Jun. 8, 2015, in PCT Application No. PCT/EP2014/053903, 17 pp.
Office Action dated Oct. 10, 2017 in Patent Japanese Application No. 2015-559505, 5 pp.
Written Opinion of the Intl. Search Authority dated Jun. 17, 2014, in PCT/EP2014/053903, 4 pp.
English Translation of International Preliminary Report on Patentability in PCT/EP2014/053903, 4 pp.
Office Action dated Oct. 30, 2013, in German Patent Application 10 2011 203 449.0, 13 pp.

METHOD AND DEVICE FOR CONTROLLING A COMPUTER PROGRAM BY MEANS OF AN INTRAORAL SCANNER

TECHNICAL FIELD

The present invention relates to a computer program as well as a method and a device for controlling the computer program by means of an intraoral scanner. In addition, the invention relates to a data medium that stores the computer program according to the invention. Furthermore, the invention relates to the use of an intraoral scanner for controlling a computer program and a device that comprises an intraoral scanner and is designed to generate a control signal when an optical marker is detected by the intraoral scanner.

PRIOR ART

Intraoral scanning systems enable a dentist to create three-dimensional representations of the oral cavity by means of a continuous recording method or by recording a few individual images. The head of a handheld camera is therefore guided at a small distance over the teeth to be recorded. A three-dimensional model can be created from the data compiled by means of the camera by using CAD/CAM software (computer aided design/computer aided manufacturing). This can then be used as the basis for a reconstruction.

When using such intraoral scanning systems, the dentist performing the work will typically have the intraoral scanning camera in his hand, be wearing gloves and come in contact with the patient's oral cavity, so that the glove is wetted with saliva or blood. If the dentist would like to operate the CAD/CAM software at the same time, he will be soiling the mouse, keypad or touchscreen of the computer executing the software with his hands, and may even introduce microorganisms from there into the patient's mouth. There are no known methods for non-contact control of CAD/CAM software that do not require control via an input interface on the respective computer system. Voice control is not available for such systems because it is susceptible to problems due to the mouth protection worn by the dentist and ambient noise that cannot be avoided in a dentist's office, and it would have to be learned first, if necessary.

The object of the present invention is therefore to permit a non-contact control of software in the dental medical field, in which the dentist need not take the camera or another scanner out of his hand.

DESCRIPTION OF THE INVENTION

This object is achieved by the method according to the invention for controlling a computer program, wherein when an optical marker is detected by an intraoral scanner, and a control signal is sent to the computer program and switches the computer program to a predetermined state. The scanner is in particular a 2D camera or a 3D scanner. The computer program is a CAD/CAM program.

The predetermined state is selected from the group consisting of a change in an image field, deletion of an image region, an image calculation, a restoration calculation and input of a patient's name. It is possible in this way for the dentist to control the functions of the CAD/CAM program without taking the intraoral scanner out of his hand. Thus, for example, when recording an image, he can change the image field by aiming the intraoral scanner at a marker assigned to this state. It is also possible for him in this way to change the image field by aiming the intraoral scanner at a marker assigned to this state. Thus it is also possible for him to change between detection of an image field and deletion of an image region. A three-dimensional image calculation or a dental restoration calculation can also be started in this way. It is preferable here for the optical marker to be applied to a carrier that has at least one optical marker. In his work, the dentist may have, for example, a tablet with optical markers for all predetermined states so that he can switch them by aiming the intraoral scanner at the marker assigned to the respective state. Additional optical markers can be applied to patient files, for example, so that it is possible to enter a patient's name into the computer program by aiming the intraoral scanner at the marker on the patient's file. According to the invention, such a marker on the patient's file can also be recognized by other computer programs used in the dentist's practice. Thus for example, a camera in a smartphone or tablet computer can scan the marker with the help of a corresponding application (app) and enable the dentist to access a patient data record directly, e.g., to access this case locally or over the Internet, or to open the respective patient files in radiology software or the doctor's practice/patient administration software associated with the marker.

The optical marker is preferably a two-dimensional barcode. This can be generated by the software itself or imported. It is also possible to learn the barcode on the basis of an externally generated label, by scanning this label once with the intraoral scanner. Such an externally generated label may originate from patient administration software, for example. In this embodiment of the invention, the patient file is prepared in paper form at the start of a treatment, the doctor passes the intraoral scanner over a binary code affixed thereto, and the corresponding patient is automatically opened in the computer program. Such a barcode can be printed out on any 2D label printer so that it can then be affixed to the patient file.

In addition, it is possible according to the invention for the optical marker to be applied to a scan body or to consist of a scan body. This may be, for example, a scan body provided with a binary code as described in US 2008/0233537 A1. To determine the type of implant in a jaw, the user must manually select the correct type of implant with traditional CAD/CAM scans of the corresponding area in the software. To determine the position of an implant, algorithms are usually used that search for certain three-dimensional structures of an attached scan body in the scan data and then determine the position and orientation of the implant beneath it. If the scan body is used as an optical marker because of its color and/or patterning, for example, then the type of implant underneath can be determined automatically according to the invention. It is also possible to apply an optical marker to the surface of the scan body, for example in the form of a two-dimensional barcode. In addition to switching the computer program to a state in which the implant corresponding to the scan body is incorporated into the data record detected, it is also possible according to the invention, for example, to switch the computer program to a state in which a scan is performed with a different resolution, preferably higher, than in other areas of the mouth. In addition, it is possible in this way to switch the computer program to a construction mode or to start a proposal calculation. Such a proposal calculation enables in particular automatic generation of a single tooth abutment in reduced form, of a single tooth abutment in full contour, of a post element for a bar or a bridge affixed by screw, or a decision about single-layer or multi-layer restoration. The scan body can also be applied to gingiva, and upon detection of the scan body or an optical marker on the scan body, the computer program is switched to a state in which a drilling location is marked or defined in a drilling template to be constructed following a model scan. The method according to the invention thus enables the use of an intraoral scanner for controlling a computer program.

The invention also relates to a computer program, in particular a CAD/CAM program, which can be controlled by means of the method according to the invention. The computer program is preferably set up to display at least one optical marker on a monitor, wherein the optical marker has an inscription indicating a state of the computer program to which the computer program can be switched by detection of an optical marker by an intraoral scanner. It is therefore possible to display optical markers for controlling the computer program, for example on the monitor of a CAD/CAM system, so that the dentist can detect the markers there using the intraoral scanner. Alternatively, the display may also be shown on a separate system, such as a tablet computer, for example. The inscription shows the dentist, by means of a text or a graphic, the state to which the computer program is switched when it guides the intraoral scanner over the corresponding optical marker. In contrast with providing the optical marker on an analog medium, it is possible here to create a menu structure so that by selecting one optical marker, some optical markers are hidden and other optical markers are shown, so that the optical markers for controlling the computer program can be presented to the dentist in an understandable manner.

The invention additionally relates to a data medium which stores the computer program according to the invention.

Furthermore, it relates to a device for controlling a computer program which comprises a carrier on which at least one optical marker is arranged. The carrier may be, for example, a laminated accompanying document. Each optical marker has an inscription which indicates a state of the computer program to which the computer program can be switched by detection of an optical marker by an intraoral scanner. The optical marker here is preferably a two-dimensional barcode.

An intraoral scanner and a computing device on which a computer program according to the invention is running can be provided as a set according to the invention. This set preferably also includes a device according to the invention for controlling the computer program.

A device which comprises an intraoral scanner may be designed according to the invention to generate a control signal when an optical marker is detected by the intraoral scanner.

BRIEF DESCRIPTION OF THE DRAWINGS

Exemplary embodiments of the invention are depicted in the drawings and explained in greater detail in the following description.

EXEMPLARY EMBODIMENTS

Figure 1:
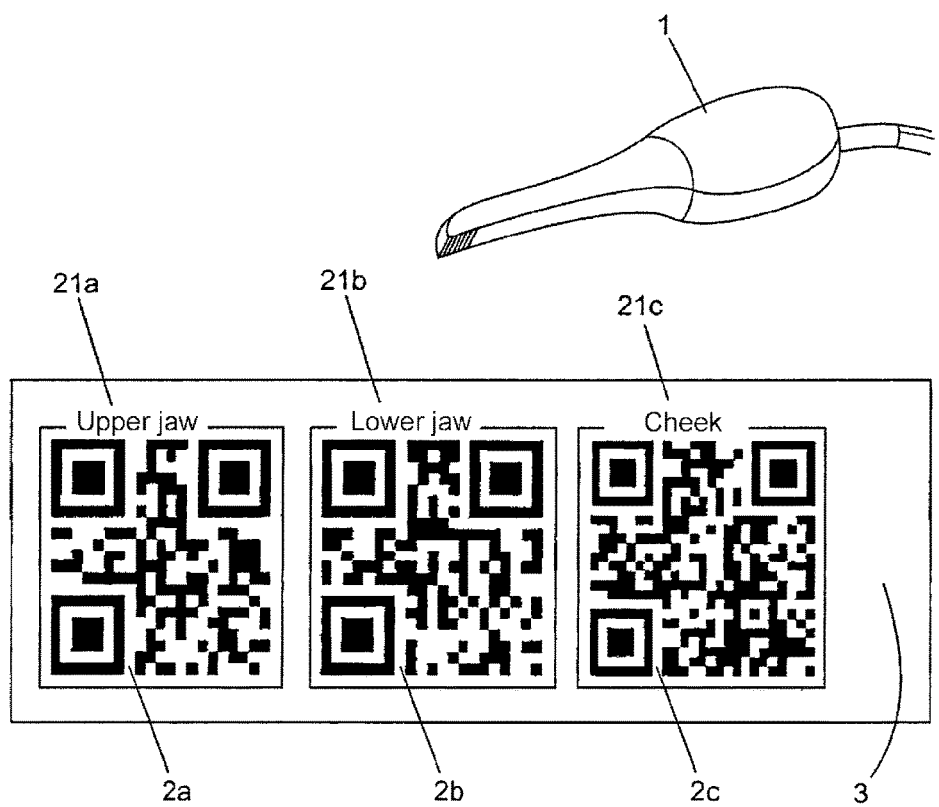
FIG. 1 shows an intraoral camera and a device for controlling a computer program for use in an embodiment of the method according to the invention.
Figure 2:
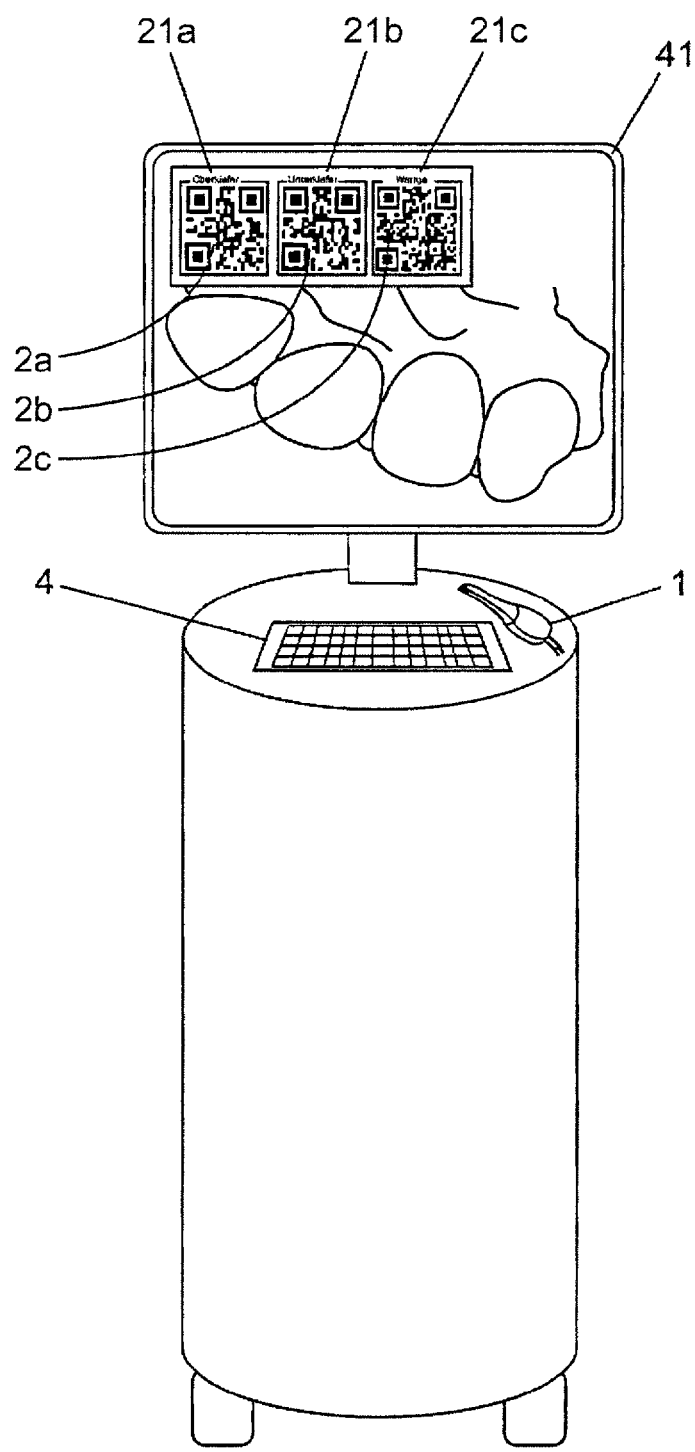
FIG. 2 shows several two-dimensional barcodes that are generated on a monitor by a computer program according to one embodiment of the invention.

In one embodiment of the invention, a CAD/CAM program runs on a device for digital molding and production of dental restorations (for example, CEREC AC+MC XL of the applicant). An intraoral 3D camera 1, which is shown in FIG. 1, serves as the scanning system for digital molding. The CAD/CAM program is set up to switch between different states such as, for example, detection of an image field, deletion of an image region, an image calculation, a restoration calculation and input of a patient's name when the intraoral camera 1 detects an optical marker in the form of a two-dimensional barcode 2a, 2b, 2c. A two-dimensional barcode 2a, 2b, 2c is applied to a laminated sheet 3 to trigger a switched state. Each two-dimensional barcode 2a, 2b, 2c has an inscription 21a, 21b, 21c, from which a dentist can ascertain the switching process to which the respective two-dimensional barcode 2a, 2b, 2c is assigned. The laminated sheet 3 serves as a device for controlling the CAD/CAM program and can be placed by the dentist on a work surface during digital molding, or can be brought onto the monitor of the CAD/CAM system. The CAD/CAM program is also set up to display the two-dimensional barcodes 2a, 2b, 2c for switching the predetermined states on a monitor 41 of a CAD/CAM system 4 together with the inscription 21a, 21b, 21c. This is illustrated in FIG. 2. The CAD/CAM system 4 is designed to generate a control signal when an optical marker is detected by the intraoral camera.

Figure 3:
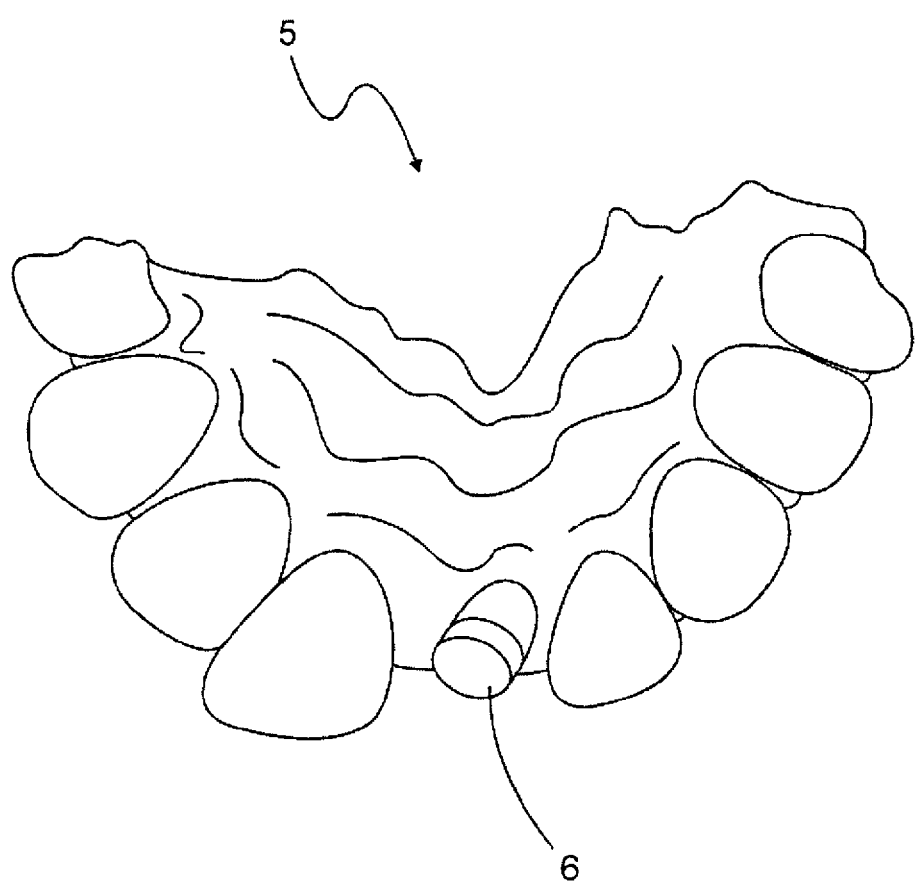
FIG. 3 shows the arrangement of a scan body in a jaw in one embodiment of the invention.

In addition, the CAD/CAM program is set up to switch to a predetermined state when it discerns a scan body 6 detected by the intraoral camera 1 in a jaw 5 shown in FIG. 3, the scan body being arranged as an implant extension on an implant located in the jaw 5 beneath the scan body 6. Upon the detection of the scan body 6, the CAD/CAM program is switched to a state that can be predetermined by the dentist. This can be, for example, a state in which a triangulated network derived from the scan undergoes a different resolution than the other image data derived from the scan.

The recognition of a two-dimensional barcode 2a, 2b, 2c or a scan body 6 in an image detected by the intraoral 3D-camera 1 is done by means of an image filter method and/or an analytical method which searches for known optical markers in the image by means of a comparison operation such as the creation of a differential image in the image space, a transmission into the frequency space, a search for similar patterns, frequencies or signals, or a statistical method.

If a barcode 2a, 2b, 2c or a scan body 6 is recognized as an optical marker in the image data, then a function assigned to the optical marker is started on the basis of a decision table stored in the computer program. If no optical marker is recognized in the image data, then, as long as a scan mode of the intraoral 3D camera 1 is active, the image data is forwarded to a scan process taking place in the computer program, such as a three-dimensional scatter plot or depth image scan process, where the image data is stored for a later three-dimensional reconstruction and a model calculation.

Figure 4:
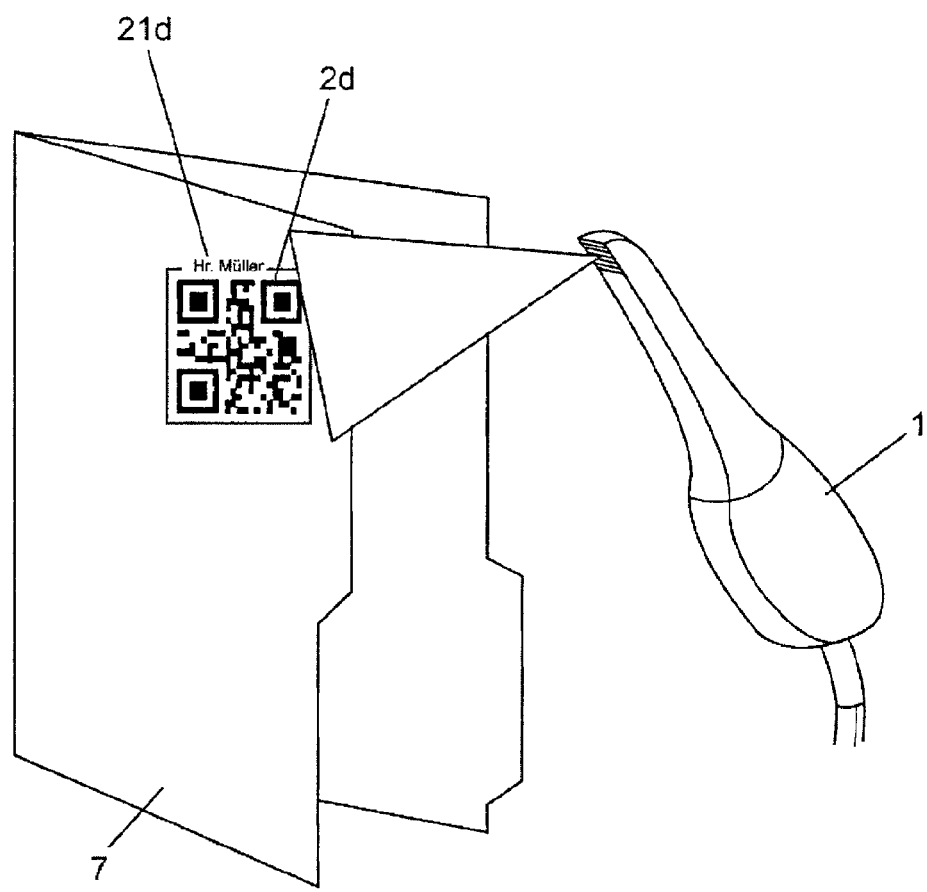
FIG. 4 shows the arrangement of a two-dimensional barcode of a patient file in one embodiment of the invention.

Switching the CAD/CAM program to a state in which data detected by the intraoral camera 1 is assigned to a certain patient is possible in this embodiment of the invention in that the intraoral camera 1 is aimed at a two-dimensional barcode 2d that has been provided with an inscription 21d and is applied to a patient file 7. This is shown in FIG. 4.

When a restoration is prepared based on the data from a CAD/CAM program that is sent back to a dentist from the dental technical laboratory, it is possible to also provide this data with a two-dimensional barcode 2 which bears a patient/restoration ID in which such a barcode accompanies the restoration or is affixed to the packaging. The dentist receiving the restoration work can then enter the barcode 2 with the intraoral camera 1 and reopen the order, previously transferred digitally to the laboratory, in the CAD/CAM program without having to perform a manual input into the CAD/CAM program.

According to this embodiment of the invention as well as the method for controlling the same, the CAD/CAM program thus permits non-contact control of a CAD/CAM software in conjunction with the barcodes 2a, 2b, 2c displayed on a carrier 3 as the device for controlling the computer program, or the barcodes 2a, 2b, 2c displayed on a monitor 41 as well as barcodes 2d optionally displayed on a patient file 7 during which the dentist need not take the intraoral camera 1 out of his hand.

The invention claimed is:

1. A method of controlling a CAD/CAM computer using an intraoral camera, comprising:
scanning an optical marker using an intraoral camera;
generating a control signal corresponding to the optical marker;
automatically selecting a predetermined operating state for a CAD/CAM computer program of the CAD/CAM computer based on the generated control signal; and
switching the CAD/CAM computer program to the predetermined operating state.

2. The method according to claim 1, wherein the scanned optical marker is a two-dimensional barcode.

3. The method according to claim 1, wherein the scanned optical marker is located on a carrier that includes another optical marker.

4. The method according to claim 1, wherein the scanned optical marker is located on a scan body.

5. The method according to claim 1, wherein the scanned optical marker is a scan body located in a patient's oral cavity.

6. The method according to claim 1, wherein the predetermined operating state for the CAD/CAM computer program is one of: detection of an image field, deletion of an image region, an image calculation, a restoration calculation, or input of a patient's name.

7. A method of operating a CAD/CAM computer, comprising:
receiving image data from an intraoral camera corresponding to an image captured by the intraoral camera;
identifying an optical marker within the image data from the intraoral camera;
generating a control signal corresponding to the optical marker;
automatically selecting a predetermined operating state for a CAD/CAM computer program of the CAD/CAM computer based on the generated control signal; and
switching the CAD/CAM computer program to the predetermined operating state.

8. The method according to claim 7, wherein the predetermined operating state is one of: detection of an image field, deletion of an image region, an image calculation, a restoration calculation, or input of a patient's name.

9. The method according to claim 7, wherein the identified optical marker is a scan body.

10. The method according to claim 9, wherein the scan body has a pattern or a color that are detectable by the intraoral camera and correspond to a type of the scan body.

11. The method according to claim 7, wherein the identified optical marker is located on a scan body.

12. The method according to claim 7, wherein the identified optical marker is located on gingiva, and
wherein the predetermined operating state is one in which a drilling location is defined in a drilling template.

13. The method according to claim 7, wherein the identified optical marker is located on a carrier that includes another optical marker.

14. The method according to claim 7, further comprising:
causing a display device to display a plurality of optical markers and a plurality of inscriptions respectively corresponding to the plurality of optical markers.

15. A dental imaging system, comprising:
an intraoral camera configured to capture an image; and
a CAD/CAM computer configured to receive image data from the intraoral camera corresponding to the image,
wherein the CAD/CAM computer is configured to:
identify an optical marker within the image data from the intraoral camera,
generate a control signal corresponding to the optical marker,
automatically select a predetermined operating state for a CAD/CAM computer program of the CAD/CAM computer based on the generated control signal, and
switch the CAD/CAM computer program to the predetermined operating state.

16. The dental imaging system according to claim 15, further comprising:
a display device,
wherein the CAD/CAM computer is further configured to cause the display device to display the optical marker.

17. The dental imaging system according to claim 16, wherein the CAD/CAM computer is further configured to cause the display device to display a plurality of optical markers respectively corresponding to a plurality of different predetermined operating states.

18. The dental imaging system according to claim 15, wherein the predetermined operating state is one of: detection of an image field, deletion of an image region, an image calculation, a restoration calculation, and input of a patient's name.

19. The dental imaging system according to claim 15, further comprising:
a carrier that includes the optical marker, another optical marker, and a plurality of inscriptions corresponding to the optical marker and the other optical marker, respectively.

* * * * *